United States Patent
Maeda et al.

[19]

[11] Patent Number: 6,146,666
[45] Date of Patent: Nov. 14, 2000

[54] *THIOBACILLUS THIOOXIDANS* GROWTH INHIBITOR

[75] Inventors: Terunobu Maeda, Ibaraki-ken; Atsunori Negishi, Tsukuba; Yasuo Nogami; Tsuyoshi Sugio, both of Okayama, all of Japan

[73] Assignee: Hazama Corporation, Tokyo, Japan

[21] Appl. No.: 09/077,368

[22] PCT Filed: Apr. 17, 1997

[86] PCT No.: PCT/JP97/01323

§ 371 Date: May 26, 1998

§ 102(e) Date: May 26, 1998

[87] PCT Pub. No.: WO98/14062

PCT Pub. Date: Apr. 9, 1998

[30] Foreign Application Priority Data

Sep. 30, 1996 [WO] WIPO ................. PCT/JP96/02838

[51] Int. Cl.[7] ............... A01N 59/16; A61L 2/23; C04B 14/34; C04B 14/30
[52] U.S. Cl. ............ 424/617; 424/646; 514/492; 514/501; 422/28; 523/122; 106/15.05; 106/664; 504/151; 504/152
[58] Field of Search ................. 424/646, 617; 514/492, 501; 422/28; 523/122; 106/15.05, 664; 210/764; 504/151, 152

[56] References Cited

U.S. PATENT DOCUMENTS

| 4,999,049 | 3/1991 | Balderson et al. | 75/234 |
| 5,096,450 | 3/1992 | Sugimura et al. | 445/50 |

FOREIGN PATENT DOCUMENTS

| 4-149053 | 5/1992 | Japan . |
| 8-208414 | 8/1996 | Japan . |

OTHER PUBLICATIONS

Aldrich Catalog, Aldrich Chemical Co., St. Louis, 1992, pp. 1271, 1272, 246, 1127.
Chemical Abstracts 99:209469y (1983).

*Primary Examiner*—John Pak
*Attorney, Agent, or Firm*—Darby & Darby

[57] ABSTRACT

A *Thiobacillus thiooxidans* growth inhibitor containing as the active ingredient at least one substance selected from the group consisting of a tungsten powder and tungsten compounds. Under acidic conditions of pH value of 4 or less, this growth inhibitor sufficiently inhibits the growth of *T. thiooxidans*. When added in a very small amount to, for example, a structural material such as concrete in a sewage disposal plant, etc., it can therefore inhibit the growth of *T. thiooxidans* without substantially decreasing the strength, etc. of the structural material per se.

14 Claims, 7 Drawing Sheets

THIOBACILLUS THIOOXIDANS GROWTH INHIBITOR

This application is a 371 of PCT/JP97/01323, filed on Apr. 17, 1997.

FIELD OF ART

The present invention relates to a *Thiobacillus thiooxidans* growth inhibitor, particularly relates to a growth inhibitor capable of inhibiting growth of *Thiobacillus thiooxidans* in sewage-treating facilities to prevent deterioration of concrete structures or concrete sewer pipes contacting sewage.

BACKGROUND OF THE INVENTION

It has been a problem that concrete structures in sewage-treating facilities become gypsiferous and deteriorated. This deterioration is known to be ascribable to sulfur-oxidizing bacteria of the genus Thiobacillus which oxidize hydrogen sulfide to sulfuric acid. These bacteria usually live widely in soil or water and grows by oxidation of sulfur compounds and assimilation of carbon dioxide. The sulfur-oxidizing bacteria of the genus Thiobacillus are known to exist not only in the portion of structures contacting sewage, but also in structures in the sewage-treating facility facing to the air but not contacting sewage, depending on the species thereof.

Various methods have been proposed for preventing such deterioration of the structures. Most of practically performed methods include coating the structures with anti-corrosive materials. However, the coating of the anti-corrosive material can easily be damaged from pinholes or scratches, and thus has problem in durability. In addition, coating on a joint of small-diameter tubes is difficult. Further, this method is not advantageous in terms of cost.

Then, another method is proposed in Japanese Laid-open Patent Application No.4-149053, in which deterioration of the structural materials due to the sulfur-oxidizing bacteria of the genus Thiobacillus is prevented by directly admixing to concrete a particular metal or a particular metal oxide insoluble in water but soluble in sulfuric acid, such as nickel, instead of coating the surface of the structures with the anti-corrosive materials. In this method, nickel completely prevents sulfur oxidation activity, respiration, and carbon dioxide gas-fixing activity of the sulfur-oxidizing bacteria when pH value is around neutrality. This method is excellent for sufficiently preventing deterioration due to the sulfur-oxidizing bacteria.

However, for practically inhibiting the growth of the sulfur-oxidizing bacteria to prevent deterioration of the concrete by adding nickel to the concrete, about 0.1 parts by weight of nickel is being added to 100 parts by weight of cement. It is therefore desired to develop an inhibitor that exhibits an excellent effect in inhibiting growth of sulfur-oxidizing bacteria in smaller adding amount.

It is known that molybdenum, ammonium molybdate or a mixture of ammonium molybdate and tungsten activates growth of *Thiobacillus novellus*, whereas tungsten, when used alone, inhibits growth of the same bacteria (Journal of Bacteriology, Vol.153, No.2 (1983) William M. et al. "Sulfite Oxidase Activity in *Thiobacillus novellus*" p.941–944). On the other hand, it is also reported that, although molybdenum ($Mo^{4+}$) activates growth of *Thiobacillus novellus* as noted above, it inhibits growth of *Thiobacillus thiooxidans* (Chemical Abstracts, Vol. 95, No.1 (Jul. 6, 1981) p127 (1081a)). Thus, even the sulfur-oxidizing bacteria of the same genus Thiobacillus have different growth inhibitory mechanism. Therefore, even if a certain growth inhibitor is recognized to have an effect on sulfur-oxidizing bacteria existing in neutral pH range of 6 to 8 such as *Thiobacillus novellus*, such an inhibitor is not used in acidic pH range of 2 to 6, in which *Thiobacillus novellus* scarcely exists. Further, it is not believed that a substance which inhibits growth of the aforementioned *Thiobacillus novellus* equally inhibits growth of sulfur-oxidizing bacteria of the genus Thiobacillus existing in pH range of 2 to 6 such as *Thiobacillus thiooxidans*.

Therefore, growth inhibitors proposed hitherto are not always effective to all of the sulfur-oxidizing bacteria of the genus Thiobacillus.

DISCLOSURE OF THE INVENTION

It is an object of the present invention to provide a *Thiobacillus thiooxidans* growth inhibitor that can sufficiently inhibit growth of *Thiobacillus thiooxidans* under the acidic condition at pH 4 or lower.

It is another object of the present invention to provide a *Thiobacillus thiooxidans* growth inhibitor that can inhibit *Thiobacillus thiooxidans* by admixing a very small amount of the inhibitor to a structural material such as concrete in a sewage-treating facility, and that does not substantially decrease strength of the structural material itself.

The present inventors proposed in Japanese Laid-open Patent Application No.4-149053 a method for preventing deterioration of a structural material due to the sulfur-oxidizing bacteria of the genus Thiobacillus. In the method, specific metals or specific metal oxides insoluble in water but soluble in sulfuric acid, such as nickel, are directly admixed to concrete. As to *Thiobacillus thiooxidans* existing in neutral to acidic pH range of 2 to 6, sufficient growth inhibitory activity is obtained at the portion of the structural material directly contacting sewage to be kept in neutral pH range. However, the present inventors found out that inhibition of growth of the same *Thiobacillus thiooxidans* is reduced on the surface of the structural material near the sewage-treating facility but not in direct contact with the sewage under the acidic condition at pH 4 or lower due to hydrogen sulfide in the air. It is not clear why the inhibition of the growth of the same bacteria varies depending on pH condition. However, it is assumed that the proposed nickel does not act directly on the bacteria themselves, but binds to an enzyme of the bacteria for exhibiting growth inhibitory activity, so that the binding to the enzyme is not sufficient under the acidic condition, resulting in insufficient growth inhibition. The present inventors then searched for a substance which sufficiently inhibits growth of *Thiobacillus thiooxidans*, which is ascribable to the deterioration of the concrete under the acidic condition at pH 4 or lower, and found out that tungsten and tungsten compounds effectively inhibit growth of *Thiobacillus thiooxidans* existing under the acidic condition, to thereby complete the present invention.

According to the present invention, there is provided a *Thiobacillus thiooxidans* growth inhibitor comprising at least one substance selected from the group consisting of tungsten powders and a tungsten compound.

According to the present invention, there is also provided a *Thiobacillus thiooxidans* growth inhibitor comprising at least one substance selected from the group consisting of nickel powders and nickel oxide powders, in addition to at least one substance selected from the group consisting of tungsten powders and a tungsten compound.

PREFERRED EMBODIMENT OF THE INVENTION

The present invention will be described more in detail hereinbelow.

The present inhibitor inhibits growth of *Thiobacillus thiooxidans*, which is known to be ascribable to deterioration of structural materials such as concrete, mortar or high-molecular polymers in sewage-treating facilities. The present inhibitor can effectively inhibit the growth of *Thiobacillus thiooxidans* not only on a structural material that contacts sewage directly but also on the surface of a structural material near a sewage-treating facility under the acidic condition at pH 4 or lower due to hydrogen sulfide in an air, to prevent the deterioration of the structural material.

The present inhibitor contains as an active ingredient at least one substance selected from the group consisting of tungsten powders (W); and tungsten compounds such as $W_{28}O_{58}$, $Na_2WO_4$, $CaWO_4$, $CaWO_4 \cdot H_2O$, $CaWO_4 \cdot 2H_2O$, or $5(NH_4)_2O \cdot 12WO_3 \cdot nH_2O$ (n=0 to 5). The active ingredient is assumed to bind to an enzyme of *Thiobacillus thiooxidans* under the acidic condition, particularly at pH 4 or lower, to inhibit sulfur oxidation, respiration and carbon dioxide gas-fixing of the bacteria, to thereby inhibit the growth of *Thiobacillus thiooxidans*. However, it is not known how these active ingredients bind to the enzyme of the bacteria.

When the active ingredient of the present inhibitor is in the form of powders, the diameter thereof is not particularly limited. However, it is desirable that the diameter is in a range to enable expression of the effective growth inhibition when the powders are admixed to the structural material such as concrete and to enable distribution to desirable position in the structural material upon forming of the structural material. Specifically, the diameter is desirably 0.005 to 0.2 mm. If the diameter exceeds 0.2 mm, the growth inhibitory activity may be reduced, thus being not preferable. If metal compounds soluble in water or an organic solvent, such as $Na_2WO_4$, are employed, these may be employed in the form of a solution.

The effective concentration of the present inhibitor is preferably not less than 1 $\mu$mol/l, and more preferably 10 to 100 $\mu$mol/l with respect to the growth environment for *Thiobacillus Thiooxidans*. For example, for preventing the deterioration of the concrete and mortar due to *Thiobacillus thiooxidans*, preferably 0.0001 to 0.1 parts by weight of the inhibitor may be added to 100 parts by weight of cement in the concrete or mortar. Particularly, even by addition of small amount of the inhibitor, such as 0.0001 to 0.01 parts by weight, sufficient growth inhibition effect is obtained for a prolonged period of time, compared to the conventional coating with anti-corrosive material.

The present inhibitor may further contain at least one substance selected from the group consisting of nickel powders and nickel oxide powders. With these substances contained, the inhibition of the growth of *Thiobacillus thiooxidans* in the pH range around neutrality can be improved. There is no particular limitation to the diameter of the nickel powders and the nickel oxide powders. However, the diameter is desirably 0.005 to 0.2 mm. The content of the nickel or nickel oxide powders is desirably selected so that tungsten-containing substance selected from the group consisting of tungsten powders and a tungsten compound: nickel powders and/or nickel oxide powders is in a range of 0.1 to 1.0 by weight.

The present inhibitor may be admixed in the concrete by, e.g., adding a desirable amount of the inhibitor to a concrete composition, and molding and curing the mixture in accordance with publicly known methods. Particularly, if the inhibitor material is in powder form, the material may easily and uniformly admixed in the concrete by centrifugal compacting. The centrifugal compacting may be performed in accordance with a publicly known method for producing Hume pipes. By suitably choosing the condition for the centrifugal compacting, concrete having desired inhibitor may be produced. In the centrifugal compacting, the diameter of the inhibitor is important. If the diameter is too small, the inhibitor moves with bleeding water during the centrifugal compacting and is possibly drained with the water. If the diameter is too large, the inhibitor possibly moves radially outwards upon centrifugal compacting. Thus, the diameter is preferably selected suitably from within the aforementioned preferable range.

The present inhibitor can sufficiently inhibit the growth of *Thiobacillus thiooxidans* even under the acidic condition at pH 4.5 or lower. By admixing very small amount of the present inhibitor to the structural material such as concrete in sewage-treating facilities, the growth of *Thiobacillus thiooxidans* is sufficiently inhibited for a long period of time. Further, the present inhibitor does not substantially decrease strength of the structural material itself.

EXAMPLES OF THE INVENTION

The present invention will be explained in more detail with reference to Examples and Comparative examples, but the present invention is not limited thereto.

Examples 1 to 3 and Comparative Example 1

20 ml of thiosulfate-inorganic salt medium (pH7.0) containing 0.2% sodium thiosulfate, 0.03% yeast extract, 0.3% $(NH_4)_2SO_4$, 0.05% $MgSO_4$–7 $H_2O$, 0.05% $K_2HPO_4$, 0.01% KCl and 0.001% $Ca(NO_3)_2 \cdot 4H_2O$ was inoculated with 1.0 g of corroded concrete, and kept under aerobic condition at 30° C. When pH of the medium decreased to 2.0, the medium was replaced by a fresh medium. This culturing operation was repeated five times. A yellow colony of *Thiobacillus thiooxidans* obtained by the culturing was isolated, and this isolated strain was designated as NBI-3.

To 20 ml of elemental sulfur-inorganic salt medium (pH2.5) containing 1% elemental sulfur, 0.3% $(NH_4)_2SO_4$, 0.05% $MgSO_4 \cdot 7H_2O$, 0.05% $K_2HPO_4$, 0.01% KCl and 0.001% $Ca(NO_3)_2 \cdot 4H_2O$ was added an aqueous solution containing 30 $\mu$mol/l of $Na_2WO_4$ (Example 1), 300 $\mu$mol/l of Na$_2$WO$_4$ (Example 2) or 1000 μmol/l of Na$_2$WO$_4$ (Example 3), or added nothing as a control (Comparative Example 1). With this mixture, NBI-3 strain was cultured. It is noted that Na$_2$WO$_4$ is insoluble at pH 2.5. Propagation of NBI-3 strain with the lapse of time was measured by absorbance at 660 nm. The results are shown in FIG. 1.

Figure 1:
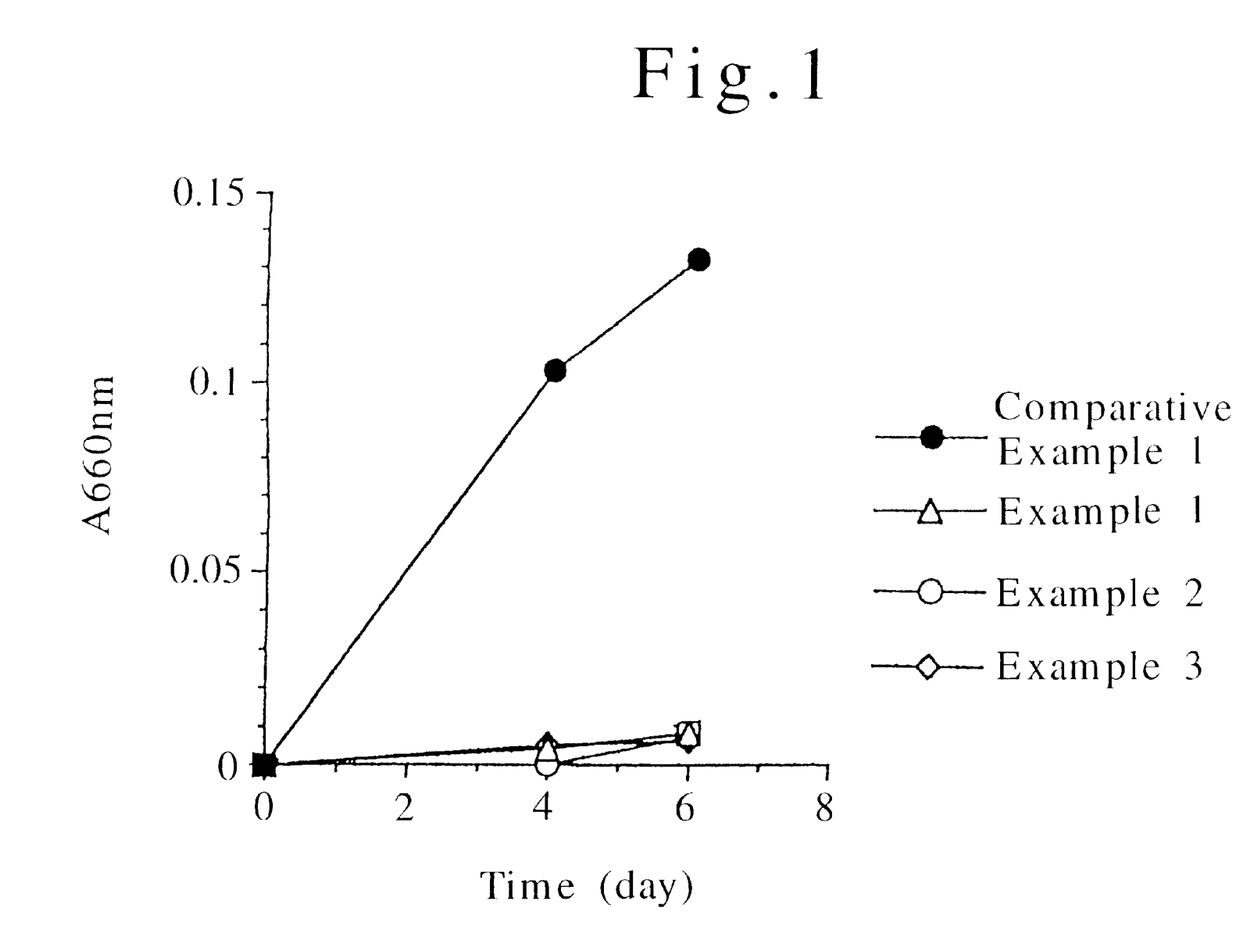
FIG. 1 is a graph showing the effect of $Na_2WO_4$ on growth of NBI-3 strain measured in Examples 1 to 3 and Comparative Example 1.

From the results of FIG. 1, it is seen that Na$_2$WO$_4$ has an excellent *Thiobacillus thiooxidans* growth inhibitory activity under acidic condition at pH2.5.

Examples 4 to 7 and Comparative Example 2

Figure 2:
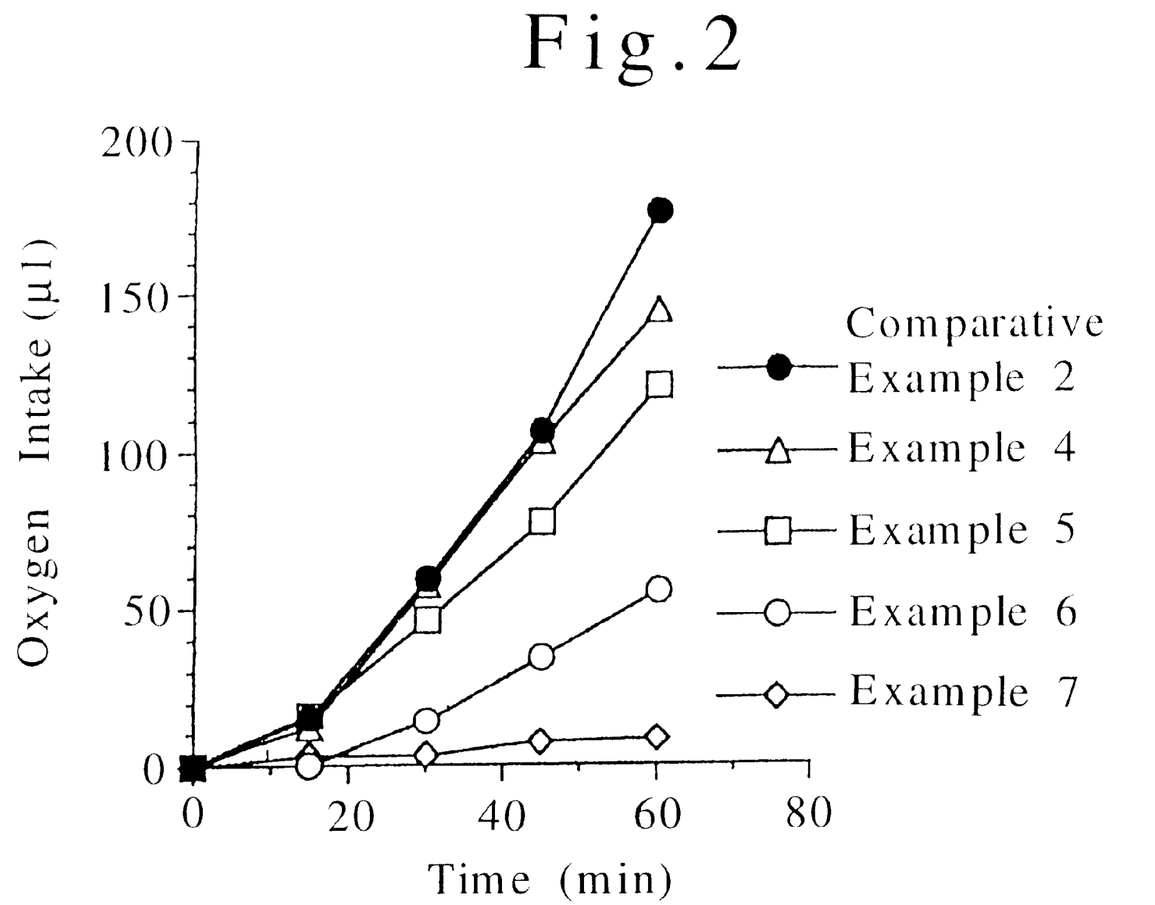
FIG. 2 is a graph showing the effect of $Na_2WO_4$ on elemental sulfur oxidation activity of NBI-3 washed cells measured in Examples 4 to 7 and Comparative Example 2.

To a reaction vessel of a Warburg manometer having a manometer, a reaction vessel and a shaker were added 5 mg of washed cells of NBI-3 cultured in Examples 1 to 3, 200 μl of β-alanine-SO$_4^{2-}$ buffer (pH3.0) and 200 μmol of sodium sulfite, which were in total volume of 3 ml. To the vessel was further added an acqueous solution containing 10 μmol/l of Na$_2$WO$_4$ (Example 4), 100 μmol/l of Na$_2$WO$_4$ (Example 5), 1000 μmol/l of Na$_2$WO$_4$ (Example 6) or 10000 μmol/l of Na$_2$WO$_4$ (Example 7), or added nothing as a control (Comparative Example 2). Intake of oxygen by the cells with the lapse of time was measured, while pH in the reaction vessel was adjusted to 3.0 with 0.2 ml of sodium hydroxide charged in the center well. The gas phase in the Warburg manometer was maintained at 30° C. with air. The results are shown in FIG. 2.

Comparative Examples 3 and 4

Measurement was performed in the same manner as in Comparative Example 2 except that boiled cells (Comparative Example 3) or non-washed cells (Comparative Example 4) were employed in place of the washed cells of NBI-3 strain. The results are shown in FIG. 3.

Comparative Examples 5 to 7

Measurement was performed in the same manner as in Examples 4 to 7 except that 1000 μmol/l of nickel of not larger than 200 mesh (Comparative Example 5), 10000 μmol/l of the same nickel (Comparative Example 6) or 20000 μmol/l of the same nickel (Comparative Example 7) was employed in place of Na$_2$WO$_4$. The results are shown in FIG. 3.

Figure 3:
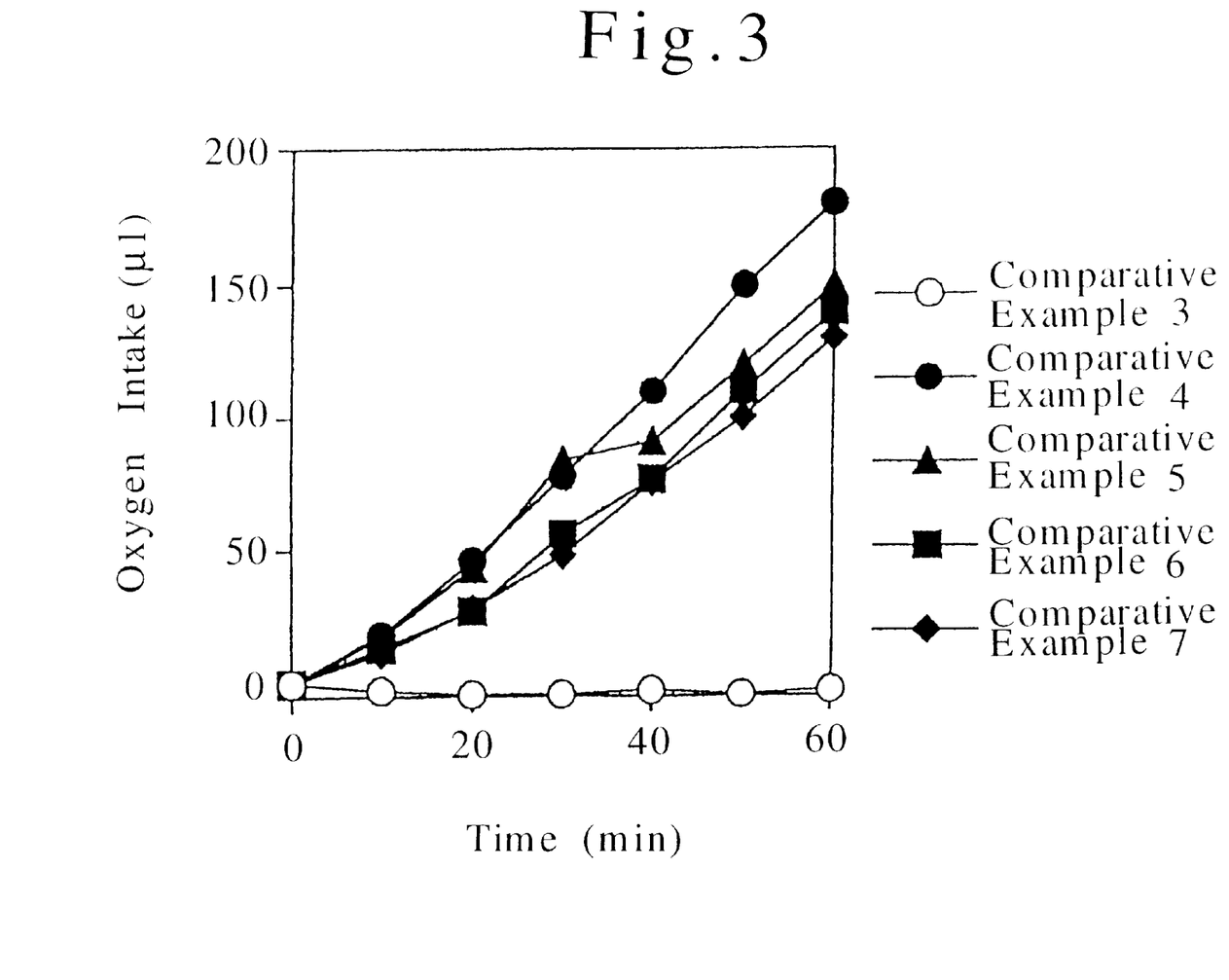
FIG. 3 is a graph showing the effect of $Na_2WO_4$ on elemental sulfur oxidation activity of NBI-3 washed cells measured in Comparative Examples 3 to 7.

Comparing the results of FIG. 3 and FIG. 2, it is seen that the Thicbacillus thiooxidans growth inhibitory effect of Na$_2$WO$_4$ is extremely greater than that of nickel in the same amount.

Examples 8 and 9 and Comparative Example 8

Figure 4:
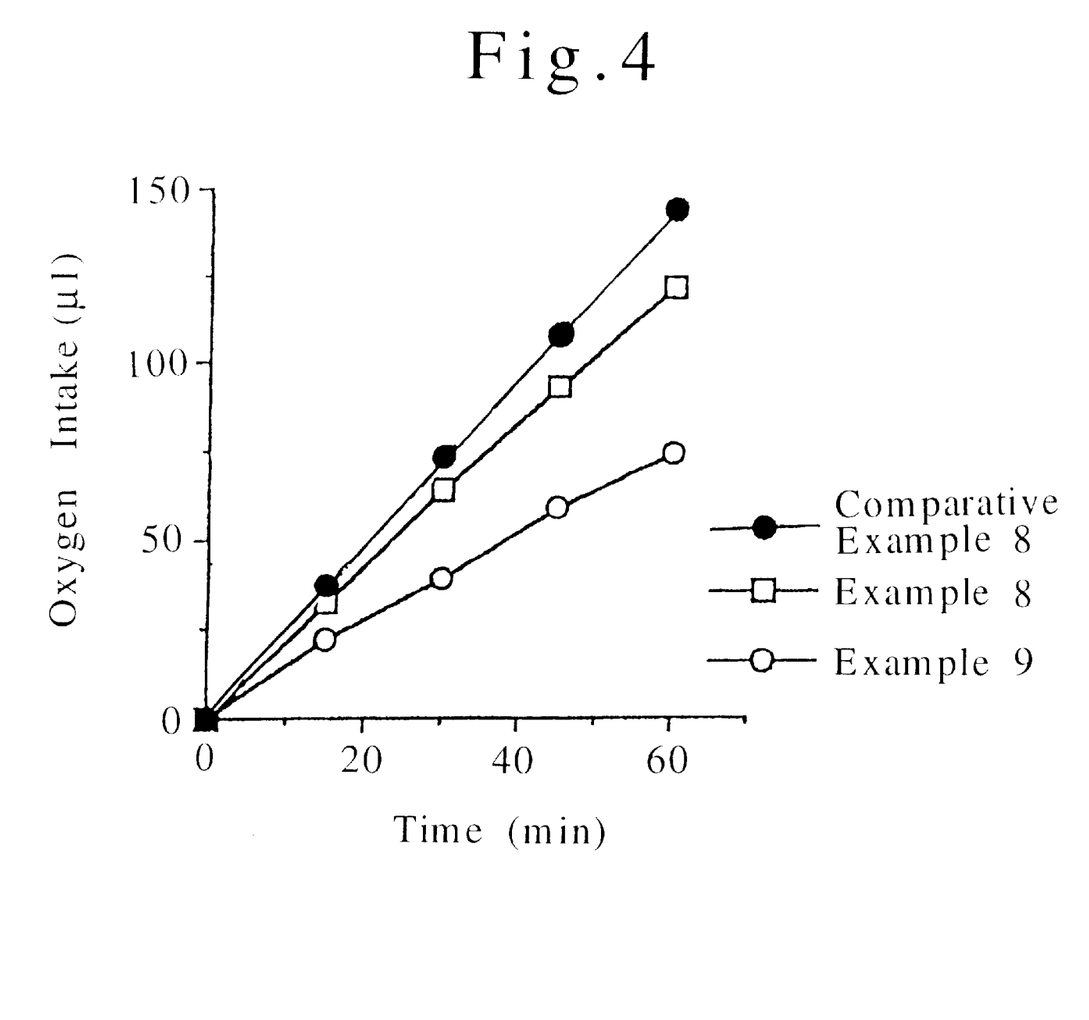
FIG. 4 is a graph showing the effect of $Na_2WO_4$ on $HSO_3^-$ oxygen activity of a membrane protein of NBI-3 strain measured in Examples 8 to 9 and Comparative Example 8.

To a reaction vessel of a Warburg manometer having a manometer, a reaction vessel and a shaker were added 1 mg of membrane protein of NBI-3 cultured in Examples 1 to 3, 200 μmol of MoPS/NaOH buffer (pH7.0) and 20 μmol of sodium sulfite. To the vessel was further added an aqueous solution containing 1000 μmol/l of Na$_2$WO$_4$ (Example 8) or 10000 μmol/l of Na$_2$WO$_4$ (Example 9), or added nothing as a control (Comparative Example 8). Intake of oxygen by the cells with the lapse of time was measured, while pH in the reaction vessel was adjusted to 7.0 with 0.2 ml of sodium hydroxide charged in the center well. The gas phase in the Warburg manometer was maintained at 30° C. with air. The results are shown in FIG. 4.

Examples 10 to 14 and Comparative Examples 9 to 13

To 20 ml of elemental sulfur-inorganic salt medium (pH2.5) containing 1% elemental sulfur, 0.3% (NH$_4$)$_2$SO$_4$, 0.05% MgSO$_4$.7H$_2$O, 0.05% K$_2$HPO$_4$, 0.01% KCl and 0.001% Ca(NO$_3$)$_2$.4H$_2$O was added an aqueous solution containing 50 μmol/l of Na$_2$WO$_4$, or added nothing as controls (Comparative Examples 9 to 13). To each of the mixtures was added *Thiobacillus thiooxidans* ON106 (Example 10), *Thiobacillus thiooxidans* ON107 (Example 11), *Thiobacillus thiooxidans* IFO13701 (Example 12), *Thiobacillus thiooxidans* JCM3867 (Example 13) or NBI-3 strain (Example 14), and cultured. Propagation of the cells of each strain was measured by absorbance at 660 nm. The results are shown in FIG. 5.

Figure 5:
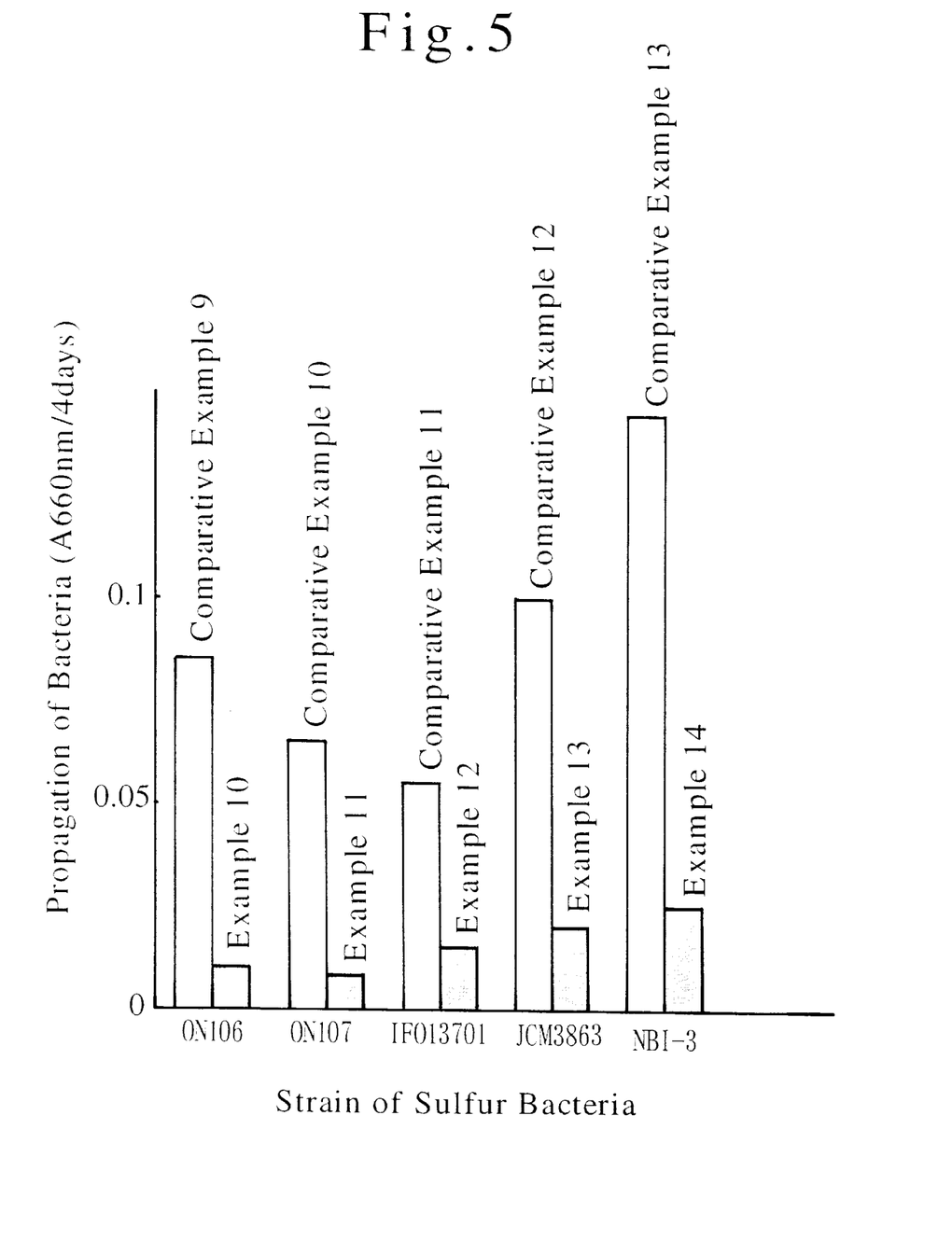
FIG. 5 is a graph showing the effect of $Na_2WO_4$ on a variety of cells measured in Examples 10 to 14 and Comparative Examples 9 to 13.

From the results of FIG. 5, it is seen that Na$_2$WO$_4$ has an excellent *Thiobacillus thiooxidans* growth inhibitory activity under the acidic condition at pH 2.5.

Examples 15 to 20 and Comparative Examples 14 and 15

To 20 ml of elemental sulfur-inorganic salt medium (pH2.5) containing 1% elemental sulfur, 0.3% (NH$_4$)$_2$SO$_4$, 0.05% MgSO$_4$.7H$_2$O, 0.05% K$_2$HPO$_4$, 0.01% KCl and 0.001% Ca(NO$_3$)$_2$.4H$_2$O was added an aqueous solution containing 100 μmol/l of tungsten (W) powders having a diameter of 10 to 50μm (Example 15), 100 μmol/l of CaWO$_4$. 2H$_2$O powders having a diameter of 10 to 25 μm (Example 16), 100 μmol/l of CaWO$_4$ powders having a diameter of 10 to 25 μm (Example 17), 100 μmol/l of W$_{28}$O$_{58}$ powders having a diameter of 10 to 25 μm (Example 18), 100 μmol/l of 5(NH$_4$)$_2$O.12WO$_3$ powders having a diameter of 10 to 25 μm (Example 19), a mixture of 100 μmol/l of Ni powders having a diameter of 10 to 50 and 100 μmol/l of W$_{28}$O$_{58}$ powders having a diameter of 10 to 25 μm (Example 20) or 100 μmol/l of Ni powders having a diameter of 10 to 50 μm (Comparative Example 14), or added nothing as a control (Comparative Example 15). With this mixture, NBI-3 strain prepared in Example 1 was cultured. Propagation of NBI-3 strain with the lapse of time was measured by absorbance at 660 nm. The results are shown in FIG. 6.

Figure 6:
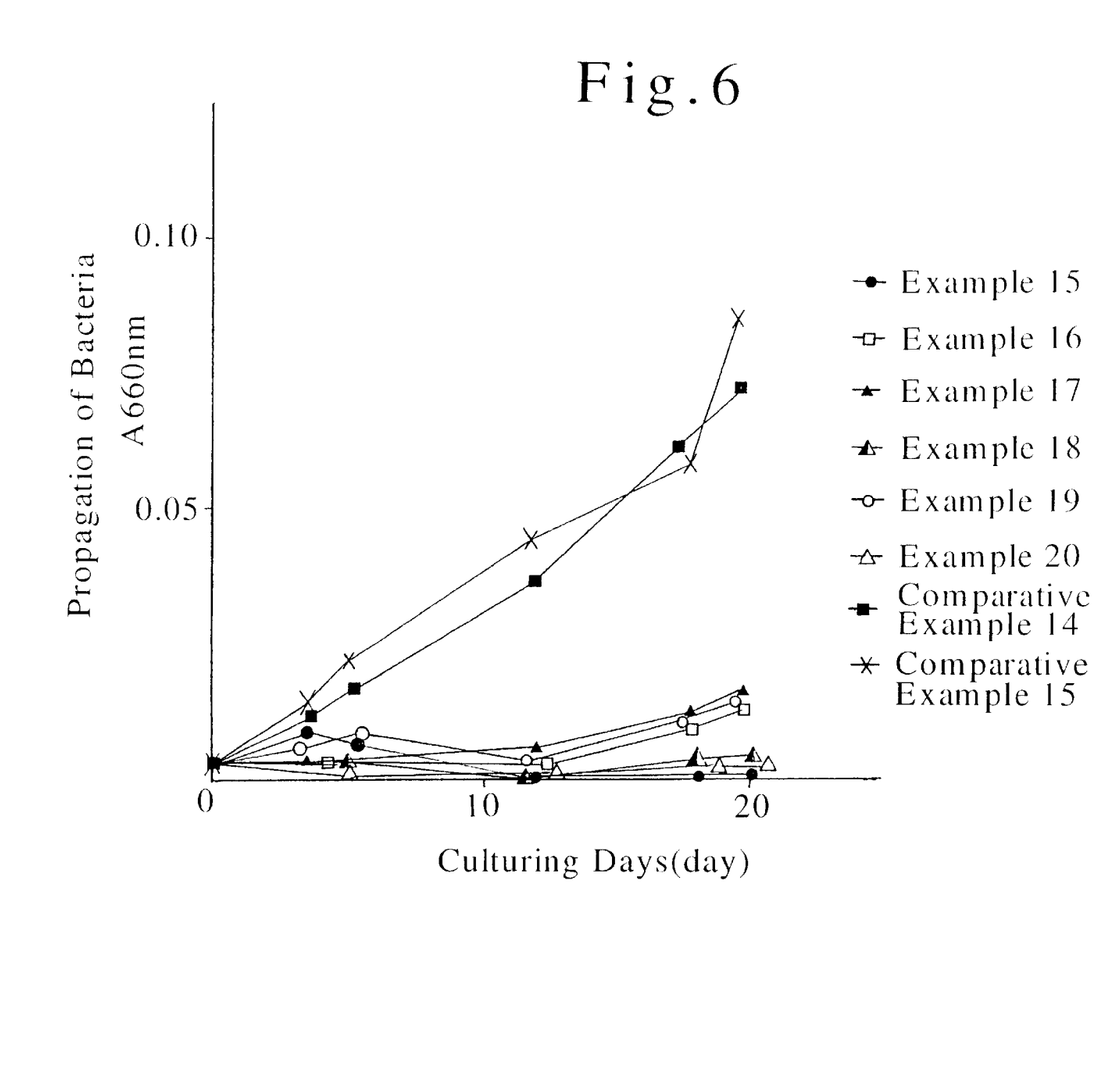
FIG. 6 is a graph showing the effect on elemental sulfur oxidation activity of NBI-3 washed cells measured in Examples 15 to 20 and Comparative Examples 14 and 15.

From the results of FIG. 6, it is seen that tungsten and various tungsten compounds have an excellent *Thiobacillus thiooxidans* growth inhibitory activity under the acidic condition at pH2.5.

Example 21 to 24

To 20 ml of elemental sulfur-inorganic salt medium (pH7.0) containing 1% elemental sulfur, 0.3% (NH$_4$)$_2$SO$_4$, 0.05% MgSO$_4$.7H$_2$O, 0.05% K$_2$HPO$_4$, 0.01% KCl and 0.001% Ca(NO$_3$)$_2$.4H$_2$O was added an aqueous solution containing 100 μmol/l of W$_{28}$O$_{58}$ powders having a diameter of 10 to 25 μm (Example 21), a mixture of 100 μmol/l of Ni powders having a diameter of 10 to 50 and 100 μmol/l of W powders having a diameter of 10 to 50 μm (Example 22), a mixture of 100 μmol/l of Ni powders having a diameter of 10 to 50 and 100 μmol/l of W$_{28}$O$_{58}$ powders having a diameter of 10 to 25 μm (Example 23) or a mixture of 100 μmol/l of Ni powders having a diameter of 10 to 50 and 100 μmol/l of 5(NH$_4$)$_2$O.12WO$_3$ powders having a diameter of 10 to 25 μm (Example 24). With this mixture, NBI-3 strain prepared in Example 1 was cultured. Propagation of NBI-3 strain with the lapse of time was measured by absorbance at 660 nm. The results are shown in FIG. 7.

Figure 7:
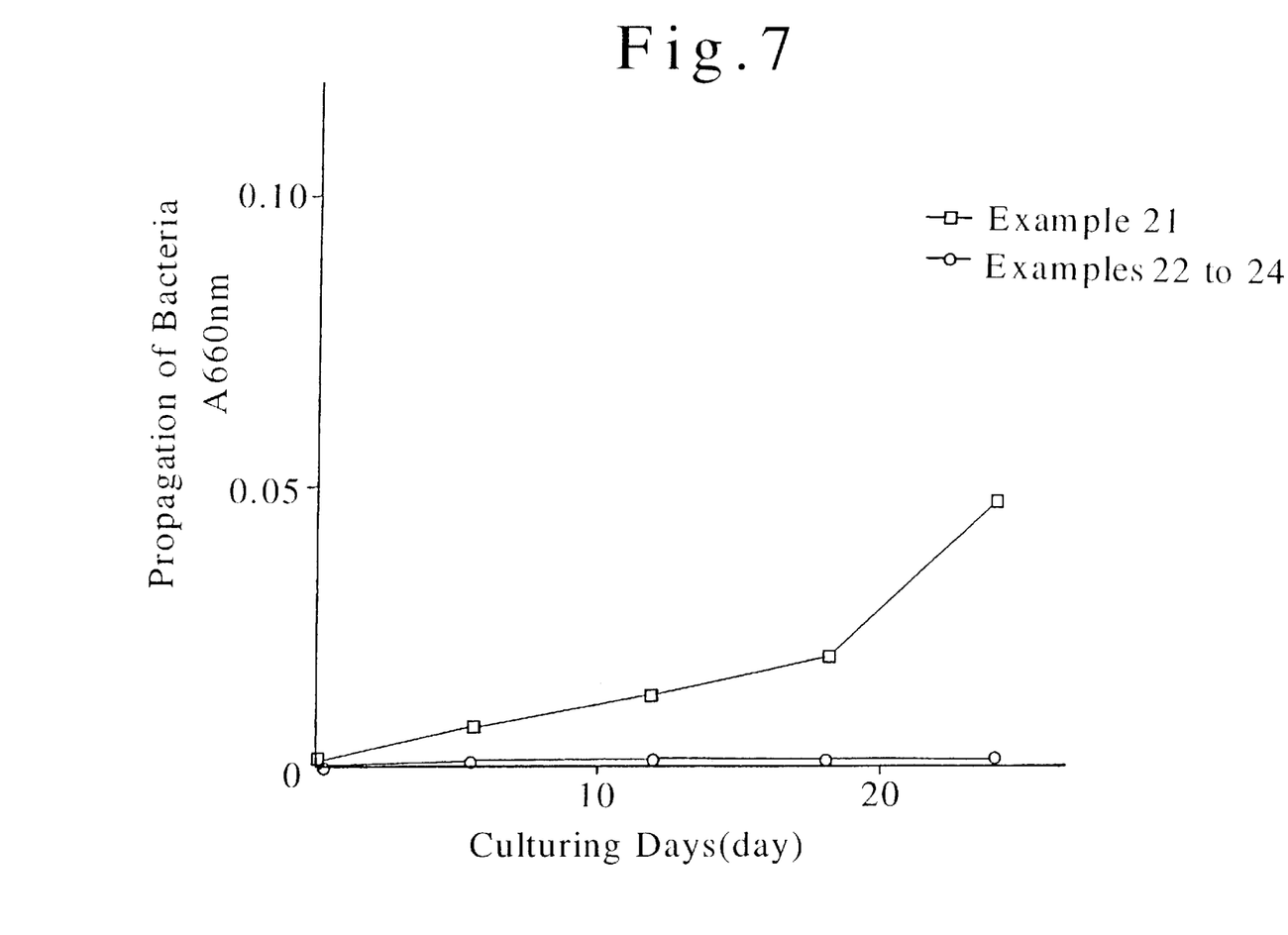
FIG. 7 is a graph showing the effect on elemental sulfur oxidation activity of NBI-3 washed cells measured in Examples 21 to 24.

From the results of FIG. 7, it is seen that the inhibitor containing nickel exhibits an excellent *Thiobacillus thiooxidans* growth inhibitory activity at pH 7.0.

Examples 25 to 27

To 20 ml of elemental sulfur-inorganic salt medium (pH2.5) containing 1% elemental sulfur, 0.3% (NH$_4$)$_2$SO$_4$, 0.05% $MgSO_4.7H_2O$, $0.05K_2HPO_4$, 0.01% KCl and 0.001% $Ca(NO_3)_2.4H_2O$ was added an aqueous solution containing a mixture of 100 μmol/l of Ni powders having a diameter of 10 to 50 and 100 μmol/l of W powders having a diameter of 10 to 50 μm (Example 25), a mixture of 100 μmol/l of Ni powders having a diameter of 10 to 50 and 100 μmol/l of $W_{28}O_{58}$ powders having a diameter of 10 to 25 μm (Example 26) or a mixture of 100 μmol/l of Ni powders having a diameter of 10 to 50 and 100 μmol/l of $5(NH_4)_2O.12WO_3$ powders having a diameter of 10 to 25 μm (Example 27). With this mixture, NBI-3 strain prepared in Example 1 was cultured. Propagation of NBI-3 strain with the lapse of time was measured by absorbance at 660 nm. As a result, propagation of NBI-3 strain was in zero level in any of Examples on the day 30.

What is claimed is:

1. A composition comprising (1) a material selected from the group consisting of concrete, mortar and high molecular weight polymers, and (2) an effective amount of a growth inhibitor for *Thiobacillus thiooxidans* selected from the group consisting of tungsten and tungsten compounds.

2. The composition of claim 1, wherein the tungsten compound is selected from the group consisting of $W_{28}O_{58}$, $Na_2WO_4$, $CaWO_4$, $CaWO_4.H_2O$, $CaWO_4.2H_2O$, $5(NH_4)_2O.12WO_3.nH_2O$, where n is 0 to 5, and mixtures thereof.

3. The composition of claim 1 wherein the diameter of the tungsten or tungsten compound is about 0.005 to 0.2 mm.

4. The composition of claim 1 wherein the concentration of the growth inhibitor is 0.0001 to 0.1 parts by weight based on 100 parts by weight of cement in said concrete or mortar.

5. The composition of claim 1 further comprising a nickel compound selected from the group consisting of nickel powders and nickel oxide powders.

6. The composition of claim 5 wherein the diameter of the nickel compound is about 0.005 to 0.2 mm.

7. A method of inhibiting the growth of *Thiobacillus thiooxidans* bacteria, comprising contacting the bacteria with an effective amount of tungsten or a tungsten compound.

8. The method of claim 7 wherein the tungsten compound is selected from the group consisting of $W_{28}O_{58}$, $Na_2WO_4$, $CaWO_4$, $CaWO_4.H_2O$, $CaWO_4.2H_2O$, $5(NH_4)_2O.12WO_3.nH_2O$, where n is 0 to 5, and mixtures thereof.

9. The method of claim 7 wherein the diameter of the tungsten or tungsten compound is 0.005 to 0.2 mm.

10. The method of claim 7 further comprising a nickel substance selected from a group consisting of nickel powders, nickel oxide powders, and mixtures thereof.

11. The method of claim 10 wherein the diameter of the nickel substance is 0.005 to 0.2 mm.

12. The method of claim 7 wherein the tungsten or tungsten compound is present in a structural material selected from the group consisting of concrete, mortar and high molecular weight polymers.

13. The method of claim 7 wherein the growth of bacteria is at a pH of about 2 to 6.

14. The method of claim 7, wherein the growth of bacteria is in a sewage treatment facility.

* * * * *

UNITED STATES PATENT AND TRADEMARK OFFICE
CERTIFICATE OF CORRECTION

PATENT NO.    : 6,146,666
DATED         : November 14, 2000
INVENTOR(S)   : Terunobu Maeda et al.

It is certified that error appears in the above-identified patent and that said Letters Patent is hereby corrected as shown below:

<u>Title page,</u>
Item [75], Inventors, "Atsunori Negishi, Tsukuba;" should be -- Atsunori Negishi, Ibaraki-Ken; --

Signed and Sealed this

Ninth Day of July, 2002

Attest:

Attesting Officer

JAMES E. ROGAN
*Director of the United States Patent and Trademark Office*